(12) United States Patent
Isobe et al.

(10) Patent No.: US 8,382,912 B2
(45) Date of Patent: Feb. 26, 2013

(54) BIOFILM-REMOVING AGENT

(75) Inventors: Kazuo Isobe, Wakayama (JP); Yuji Okauchi, Wakayama (JP)

(73) Assignee: KAO Corporation, Tokyo (JP)

( * ) Notice: Subject to any disclaimer, the term of this patent is extended or adjusted under 35 U.S.C. 154(b) by 289 days.

(21) Appl. No.: 12/742,692

(22) PCT Filed: Nov. 27, 2008

(86) PCT No.: PCT/JP2008/003487
§ 371 (c)(1),
(2), (4) Date: May 13, 2010

(87) PCT Pub. No.: WO2009/069296
PCT Pub. Date: Jun. 4, 2009

(65) Prior Publication Data
US 2010/0261631 A1 Oct. 14, 2010

(30) Foreign Application Priority Data

Nov. 28, 2007 (JP) .................. 2007-307261
Nov. 28, 2007 (JP) .................. 2007-307262

(51) Int. Cl.
*B08B 3/04* (2006.01)
*C11D 7/26* (2006.01)
*C11D 7/32* (2006.01)

(52) U.S. Cl. .......... 134/34; 510/161; 510/199; 510/383; 510/423; 510/433; 510/435; 510/488; 510/499

(58) Field of Classification Search .................. 510/199, 510/238, 383, 423, 435, 433, 488, 499, 161; 424/54; 134/42, 34
See application file for complete search history.

(56) References Cited

U.S. PATENT DOCUMENTS

| | | | |
|---|---|---|---|
| 5,759,970 A | 6/1998 | Prevost et al. | |
| 5,919,748 A | 7/1999 | Noguchi et al. | |
| 5,958,869 A | 9/1999 | Noguchi et al. | |
| 6,100,080 A | 8/2000 | Johansen | |
| 6,759,030 B2 * | 7/2004 | Kosti | 424/53 |
| 2003/0035848 A1 | 2/2003 | Batarseh et al. | |
| 2003/0150069 A1 | 8/2003 | Kleen et al. | |
| 2004/0253194 A1 | 12/2004 | Rioux et al. | |
| 2006/0058211 A1 * | 3/2006 | Aihara et al. | 510/499 |

FOREIGN PATENT DOCUMENTS

| | | |
|---|---|---|
| CN | 1161958 A | 10/1997 |
| DE | 100 20 887 A1 | 10/2001 |
| EP | 0 781 835 A1 | 7/1997 |
| EP | 0 788 832 A1 | 8/1997 |
| JP | 48-22417 A | 3/1973 |
| JP | 48-72116 A | 9/1973 |
| JP | 2-9852 A | 1/1990 |
| JP | 8-151324 A | 6/1996 |
| JP | 9-271655 A | 10/1997 |
| JP | 10-511999 A | 11/1998 |
| JP | 11-248314 A | 9/1999 |
| JP | 2001-208677 A | 7/2001 |
| JP | 2003-521472 A | 7/2003 |
| JP | 2003-522734 A | 7/2003 |
| JP | 2005-75873 A | 3/2005 |
| JP | 2007-146134 A | 6/2007 |
| WO | WO 96/20737 A1 | 7/1996 |
| WO | WO 97/30057 A1 | 8/1997 |

OTHER PUBLICATIONS

Extended European Search Report issued on Mar. 23, 2011 in corresponding European Patent Application No. 08 85 3716.
International Search Report issued on Mar. 3, 2009 for International Application No. PCT/JP2008/003487.
Chinese Office Action for Application No. 200880118000.4 dated Sep. 9, 2011 (with English translation).

* cited by examiner

*Primary Examiner* — Gregory Delcotto
(74) *Attorney, Agent, or Firm* — Birch, Stewart, Kolasch & Birch, LLP

(57) ABSTRACT

A biofilm-removing agent which effectively removes biofilms is provided.
A biofilm-removing agent containing a basic amino acid derivative represented by the following formula (1) or a salt thereof:

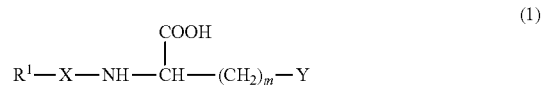

(wherein $R^1$ represents a linear- or branched-alkyl group having 4 to 18 carbon atoms or a linear- or branched-alkenyl group having 4 to 18 carbon atoms; X and Y each represent a group selected from the groups represented by the following formulas:

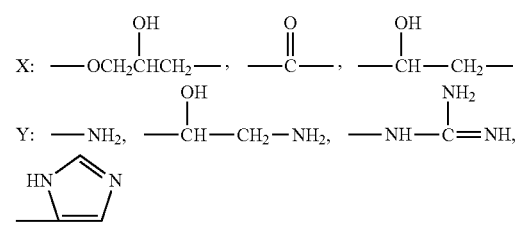

and m represents an integer from 1 to 5).

17 Claims, No Drawings

BIOFILM-REMOVING AGENT

FIELD OF THE INVENTION

The present invention relates to a biofilm-removing agent, more specifically relating to a biofilm-removing agent for use in various fields associated with microorganisms, which effectively removes biofilms and prevent hazards attributable to biofilms. This invention also relates to a cleansing composition for hard surfaces, which effectively removes a complex of contaminants such as biofilms and miscellaneous contaminants.

BACKGROUND OF THE INVENTION

Biofilm is otherwise called "biological film" or "slime", and generally denotes a structure composed of high-molecular materials (e.g., polysaccharides and proteins) produced by microorganisms which adhere to the surface of a substance and proliferate in an aqueous system. The formation of biofilm entails a dangerous consequence attributable to microorganisms, thereby giving rise to many problems in various industrial fields. For example, when formed at the inside area of a pipe to be used in a food plant, biofilms easily peel off from the inside area and foreign materials intrude into a product, and also cause a food poisoning due to toxins emanated from microorganism. Furthermore, formation of biofilms on the metallic surfaces causes metal corrosion, thus accelerating the aging of facilities.

Furthermore, most of the microorganisms responsible for the formation of a biofilm tend to spoil the efficacy imparted by a microorganisms-controlling agent (e.g., bactericides and bacteriostatic agents), compared with microorganisms that are in a dispersed or suspended state in an aqueous system. In the medical field, there have been many reports revealing that microorganisms sneak into the narrow gaps or holes of a medical instrument (e.g., endoscope) and stay therein to form biofilms, leading to in-hospital infection. It is also well known that a biofilm formed on the teeth in the human oral cavity, the so-called dental plaque, is causative of dental caries or periodontal diseases, and these problems have long been studied.

So far, the idea of not proliferating microorganisms, particularly bacteria, by subjecting the bacteria to a bactericidal action or a bacteriostatic action has been studied as a way to prevent hazards attributable to biofilms. Patent Document 1 describes an antibacterial preparation in which arginine or a derivative thereof such as arginine hydrochloride, arginine ethyl ester or arginine-glutamic acid, is mixed with a compound exhibiting antibacterial activity. However, its effects are far from satisfactory, and this document rather shows antibacterial effects against microbial aggregates, not intended for the removal of biofilms.

In order to remove biofilms, a method of using a bactericide, a method of using a chelating agent, a method of using an enzyme and the like have been attempted. Patent Document 2 discloses a method of using a hypochlorite, an alkali metal hydroxide and a surfactant in combination. However, none of these methods are sufficient to effectively remove biofilms. As such, these methods still have grave problems.

That is, in the case of using a highly bactericidal cationic surfactant or a highly bactericidal agent having a feature of rapid-acting property, such as hypochlorite, the bactericidal property is rapidly lost due to the organic substances in the system or in the biofilms. Therefore, it is difficult for these agents to maintain the bacterial count reducing effect for a long time, and when the bactericidal effect disappears, bacteria start to proliferate again. In addition, since a bactericidal agent is not intended to remove biofilms, this agent is required to start its action before microorganisms attach to a surface and form a biofilm.

As discussed above, since biofilms are formed from various substances such as fungous forms, polysaccharides and proteins, it is difficult to completely remove biofilms by decomposing merely a part of these compounds. Therefore, while a method of removing biofilms by using an enzyme as disclosed in Patent Document 3 is effective to a certain extent, it remains difficult to completely remove biofilms, and this method does not have a suppressive action on biofilms, either. Thus the bacteria that have been left behind in biofilms are liable to proliferate again, so it is inevitable for macromolecular substances such as polysaccharides or proteins to be produced.

Biofilms tend to be formed in a humidified atmosphere, such as bathroom, cooking room, kitchen, toilet bowl, drainage ditch, drain pipe and medical instrument, where microorganisms can easily proliferate. But the types of contaminants differ from one place to another. For example, most of the contaminants frequently seen in the kitchen are oils and fats, while most of the contaminants frequently seen in the bathroom are metallic soaps, particularly calcium salts of fatty acids. Meanwhile, most of the contaminants liable to adhere to in the inner side of a toilet bowl are inorganic contaminants, while most of the contaminants liable to adhere to a medical instrument are protein contaminants, such as blood and body fluid. Biofilms coexist with such contaminants to form a complex of contaminants. Therefore, a technique that is capable of removing such a complex has been sought.

Patent Document 1: JP-A-08-151324
Patent Document 2: JP-A-2005-75873
Patent Document 3: JP-A-2001-508677

SUMMARY OF THE INVENTION

The present invention provides a biofilm-removing agent containing a basic amino acid derivative represented by the following formula (1) or a salt thereof:

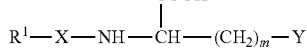

wherein $R^1$ represents a linear- or branched-alkyl group having 4 to 18 carbon atoms or a linear- or branched-alkenyl group having 4 to 18 carbon atoms; X and Y each represent a group selected from those represented by the following formulas:

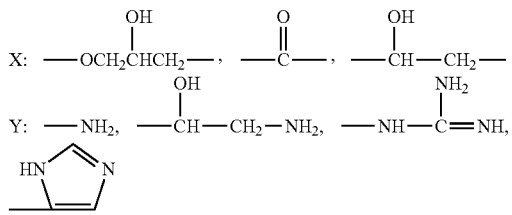

and m represents an integer from 1 to 5.

The present invention also provides a biofilm-removing agent containing an arginine derivative obtained by reacting arginine or a salt thereof with a glycidyl ether, or a salt of said derivative.

the present invention also provides a biofilm-removing agent composition containing any one of the biofilm-removing agents mentioned above and, as others, one or more members selected from the group consisting of surfactants and chelating agents.

The present invention also provides a cleansing composition for hard surfaces, containing the basic amino acid derivative represented by the formula (1) or a salt thereof, or the arginine derivative or a salt thereof.

The present invention also provides a cleansing composition for hard surfaces, containing the basic amino acid derivative represented by the formula (1) or a salt thereof, a surfactant other than the derivative or the salt, and an alkali agent.

The present invention also provides a cleansing composition for hard surfaces, containing the basic amino acid derivative represented by the formula (1) or a salt thereof and, as others, one or more selected from the group consisting of surfactants and chelating agents.

The present invention also provides a cleansing composition for medical instruments, containing the basic amino acid derivative represented by the formula (1) or a salt thereof.

The present invention also provides a method for cleansing medical instruments, which includes immersing a medical instrument in a cleansing composition for medical instruments, or placing a medical instrument in the stream of an aqueous cleansing composition, or contacting a medical instrument with an aqueous cleansing composition while exposing it to ultrasonic vibration.

The present invention also provide use of a composition as a biofilm-removing agent, wherein the composition contains the basic amino acid derivative represented by the formula (1) or a salt thereof.

The present invention also provides use of a composition as a cleansing agent for hard surfaces, wherein the composition contains the basic amino acid derivative represented by the formula (1) or a salt thereof.

The present invention also provides use of a composition as a cleansing agent for medical instruments, wherein the composition contains the basic amino acid derivative represented by the formula (1) or a salt thereof.

DETAILED DESCRIPTION OF THE INVENTION

The present invention is intended to provide a biofilm-removing agent and a biofilm-removing agent composition which effectively remove biofilms that are formed from microorganisms and microbe-produced substances in various areas, and also to provide a cleansing composition for hard surfaces and a cleansing composition for medical instruments, which effectively remove a complex of contaminants in which biofilms and various kinds of contaminants coexist.

The present inventors conducted an in-depth investigation so as to obtain a biofilm-removing agent capable of effectively removing biofilms, and thus discovered that a specific amino acid derivative had the ability to remove biofilms effectively.

According to the present invention, biofilms that are formed from microorganisms and microbe-produced substances in various areas can be effectively removed, and a complex of contaminants in which biofilms coexist with various kinds of contaminants can also be effectively removed.

Hereinafter, the present invention will be explained in more detail.

The biofilm-removing agent and the cleansing composition for hard surfaces of the present invention each contain one or more of the basic amino acid derivatives represented by the following formula (1) and/or salts thereof:

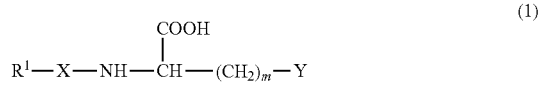
(1)

wherein $R^1$ represents a linear- or branched-alkyl group having 4 to 18 carbon atoms or a linear- or branched-alkenyl group having 4 to 18 carbon atoms; X and Y each represent any one of the groups represented by the following formulas:

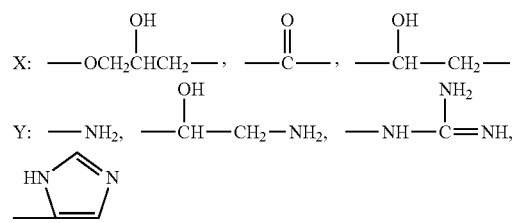

and m represents an integer from 1 to 5.

The alkyl group or alkenyl group represented by $R^1$ may be a linear chain or a branched chain, and in view of the biofilm-removing effect, the alkyl group or alkenyl group has 4 to 18 carbon atoms, preferably 6 to 14 carbon atoms, more preferably 8 to 14 carbon atoms, and even more preferably 10 to 14 carbon atoms. Specific examples include an n-hexyl group, a 2-ethylhexyl group, an n-octyl group, a decyl group, a dodecyl group, a myristyl group and the like. The alkyl group or alkenyl group represented by R1 may be provided alone or in combination. The alkyl composition may be a mixture composition of alkyls derived from a naturally occurring oil, such as palm oil and palm kernel oil.

In the formula (1), m represents an integer from 1 to 5, preferably 2 to 4, and more preferably 3. X is preferably —OCH$_2$—CH(—OH)CH$_2$—, and Y is preferably —NH—C(—NH$_2$)=NH.

Examples of the salt of the basic amino acid derivative (1) include salts of inorganic acids such as hydrochloride, sulfate and phosphate; and salts of organic acids such as acetate, lactate, citrate and an acidic amino acid salt, and preferred examples include hydrochloride, acetate, lactate and citrate.

The compound represented by the formula (1) is obtained by reacting a basic amino acid such as, for example, arginine, lysine, ornithine, histidine or hydroxyhistidine, with a compound such as a glycidyl ether, a fatty acid chloride, a fatty acid anhydride or an epoxy alkane. Preferred examples include a compound obtained by reacting arginine with a compound such as a glycidyl ether, a fatty acid chloride, an acid anhydride or an epoxyalkane, and more preferred examples include a compound of the following formula (2), obtained by reacting arginine with a glycidyl ether:

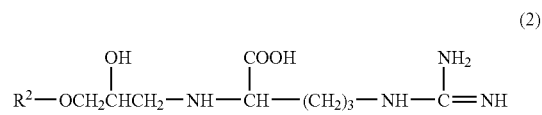
(2)

wherein $R^2$ represents a linear- or branched-alkyl group having 4 to 18 carbon atoms or a linear- or branched-alkenyl group having 4 to 18 carbon atoms.

These reaction products may include unreacted reactants and side products, to the extent that their biofilm-removing abilities are not impaired.

JP-A-09-271655 discloses a cosmetic composition and a cleansing composition containing a basic amino acid derivative or a salt thereof which is obtained by reacting a glycidyl ether with a basic amino acid or a salt thereof, but these compositions are characterized by being less irritative to the skin and mucosa, and are used to enhance the conditioning effect on the hair or the like. Thus, nothing can be anticipated or predicted from this document with regard to the effects achieved by the present invention, such as the effect of removing biofilms and the effect of removing a comlex of contaminants in which biofilms and various types of contaminants coexist.

The amount of the biofilm-removing agent and cleansing composition for hard surfaces to be used according to the present invention can be determined depending on the types of formulations and their purpose. However, in the case where the agent and the composition are made to act on biofilms, the biofilm-removing agent and the cleansing composition are usually used at an aqueous state, and the concentration is, in terms of the concentration of the compound of formula (1), preferably 0.001 to 10% by weight, more preferably 0.002 to 7% by weight, and even more preferably 0.005 to 5% by weight, from the viewpoints of cost, ease of handling and biofilm-removing ability.

The biofilm-removing agent composition and cleansing composition for hard surfaces of the present invention increase the solubility of the compound represented by the formula (1) or enhance the biofilm-removing ability. Furthermore, for the purpose of increasing the cleansing effect, one or more of members selected from the group consisting of an anionic surfactant, a nonionic surfactant, an amphoteric surfactant and a cationic surfactant can be used in combination, in addition to the compound represented by the formula (1).

Examples of the anionic surfactant include ligninsulfonic acid salts, alkylbenzenesulfonic acid salts, alkylsulfonic acid salts, polyoxyethylene (hereinafter, indicated as "POE") alkylsulfonic acid salts, POE alkyl phenyl ether sulfonic acid salts, POE alkyl phenyl ether phosphoric acid ester salts, POE aryl phenyl ether sulfonic acid salts, alkylsulfuric acid ester salts, POE alkyl ether sulfuric acid ester salts, POE aryl phenyl ether phosphoric acid ester salts, naphthalenesulfonic acid salts, naphthalenesulfonic acid-formalin condensate, POE tribenzyl phenyl ether sulfonic acid salts, alkylphosphoric acid salts, POE alkylphosphoric acid salts, POE tribenzyl phenyl ether phosphoric acid salts, dialkylsulfosuccinic acid salts, fatty acid salts (soaps), POE alkyl ether acetic acid salts, and the like. Among them, it is more preferable to use an alkylsulfuric acid ester salt, a POE alkyl ether sulfuric acid ester salt or a POE alkyl ether acetic acid salt.

Examples of the nonionic surfactant include monovalent alcohol derivative type nonionic surfactants such as POE alkyl ethers, POE alkyl phenyl ethers, polyoxypropylene-POE (block or random) alkyl ethers, POE aryl phenyl ethers, POE styrenated phenyl ethers and POE tribenzyl phenyl ethers; polyvalent alcohol derivative type nonionic surfactants such as (poly)glycerin fatty acid esters, sucrose fatty acid esters, sorbitan fatty acid esters, POE sorbitan fatty acid esters, alkyl polyglycosides and fatty acid alkanolamides; and the like. Among them, it is more preferable to use a POE alkyl ether, a (poly)glycerin fatty acid ester, an alkyl polyglycoside, a sorbitan fatty acid ester or a POE sorbitan fatty acid ester.

Examples of the amphoteric surfactant include alkylcarboxybetaine, alkylsulfobetaine, alkylhydroxysulfobetaine, fatty acid amidobetaine, alkyldimethylamine oxide and the like. Among them, it is preferable to use an alkyldimethylamine oxide or an alkylhydroxysulfobetaine.

Examples of the cationic surfactant include alkyltrimethylammonium salts, dialkyldimethylammonium salts, and the like. Among them, an alkyltrimethylammonium salt is preferred. The salt is preferably a halide, and more preferably a chloride or a bromide.

Of these surfactants, nonionic surfactants are preferred. Furthermore, these surfactants can be used in combination with the compound of the formula (1) at any ratio according to purpose. A preferred ratio is such that the weight ratio of the compound of formula (1):other surfactant is 1:99 to 99:1, more preferably 5:95 to 95:5, and even more preferably 10:90 to 80:20, from the viewpoint of the stability of the product and the cleansing effect.

The biofilm-removing agent and cleansing composition for hard surfaces of the present invention can use a chelating agent in combination for the purpose of increasing the effect. Examples of the chelating agent include aminocarboxylic acid derivatives such as nitrilotriacetic acid, ethylenediamine tetraacetic acid, iminodisuccinic acid, aspartic acid diacetic acid and aminomethylglycine diacetic acid, and/or salts thereof; salts of organic acids such as citric acid, tartaric acid and gluconic acid; polymer electrolyte-based compounds such as polyacrylic acid/maleic acid copolymers and/or salts thereof; phosphoric acid-based compounds such as tripolyphosphoric acid salts, orthophosphoric acid salts and pyrophosphoric acid salts; phosphonic acid-based compounds such as 1-hydroxyethan-1,1-diphosphonic acid and/or salts thereof, aminotri(methylenephosphonic acid) and/or salts thereof, and ethylenediaminetetra(methylenephosphonic acid) and/or salts thereof; aluminosilicic acids such as A-type zeolite and B-type zeolite; and the like. Among them, nitrilotriacetic acid salts, ethylenediamine tetraacetic acid salts, tripolyphosphoric acid salts, 1-hydroxyethane-1,1-diphosphonic acid and/or salts thereof are preferred.

These chelating agents can be used in combination with the compound of formula (1) at any ratio according to the purpose. A preferred ratio is such that the weight ratio of the compound of formula (1):chelating agent is 1:99 to 99:1, and more preferably 5:95 to 95:5, from the viewpoint of the cleansing effect.

The cleansing composition for hard surfaces of the present invention is allowed to have an alkali agent incorporated therein so that its cleansing power could improve. Examples of the alkali agents include alkali metal hydroxides such as sodium hydroxide and potassium hydroxide; silicic acid salts such as sodium orthosilicate, sodium metasilicate, sodium sesquisilicate, sodium silicate No. 1, sodium silicate No. 2, and sodium silicate No. 3; phosphoric acid salts such as sodium dihydrogen phosphate, disodium hydrogen phosphate, trisodium phosphate, and sodium pyrophosphate; carbonic acid salts such as disodium carbonate, sodium hydrogen carbonate, dipotassium carbonate and potassium hydrogen carbonate; boric acid salts such as sodium borate; salts of organic acids such as sodium acetate, potassium acetate, sodium lactate and potassium lactate; alkanolamines such as monoethanolamine, diethanolamine and triethanolamine; basic amino acids such as lysine and arginine; and polyamines such as ethylenediamine, diethylenetriamine, spermine and spermidine. Two alkali agents or more may be used in combination. Of these alkali agents, sodium hydroxide, potassium hydroxide, sodium orthosilicate, sodium metasilicate, and monoethanolamine are preferred.

The alkali agents can be used in combination at any ratio according to the purpose, provided the alkali agents are stably incorporated into the cleansing composition for hard surfaces. A preferred ratio is such that the weight ratio of the sum of the compound represented by the formula (1) and other surfactants: alkali agent is 90:10 to 1:99, and more preferably 50:50 to 10:90, from the viewpoint of the cleansing effect.

These alkali agents are used when the cleansing composition for hard surfaces of the present invention is used, so as to make the pH of the operating system alkaline. It is preferable to incorporate the alkali agents so that the pH at the concentration at the time of operation is 8.0 or higher, preferably 8.0 to 13.5, and more preferably 8.5 to 13.0.

The concentration of the compound of formula (1) in the product form of the biofilm-removing agent composition and cleansing composition for hard surfaces of the present invention can be appropriately determined depending on the differences of use and formulation. However, from the viewpoint of the difficulties in productization and effects, the concentration is preferably 0.001 to 80% by weight, more preferably 0.002 to 60% by weight, and even more preferably 0.005 to 40% by weight.

The formulation of the biofilm-removing agent, biofilm-removing agent composition and cleansing composition for hard surfaces of the present invention may be a solution dissolved in a solvent such as water, ethanol or isopropanol, or a solid, a gel form, an emulsified/dispersed form, a powdered form, an aerosol or the like, according to the use and purpose, and the formulation can be appropriately selected from these. The formulation not only may take a product form suited for the operating concentration, but also may be kept in a product form of high concentration so as to be diluted at the time of use. Alternatively, it is also possible to use the formulation by mixing the compound of the formula (1), a surfactant and/or a chelating agent at the time of use.

The biofilm-removing agent and cleansing composition for hard surfaces of the present invention may contain therein one or more of a thickening agent, a viscosity adjusting agent, a pH adjusting agent, a solvent, a fragrance, a colorant, an antioxidant, an antiseptic, a fluorescent agent, an excipient, a soil releasing agent, a bleaching agent, a bleach activating agent, a powderizing agent, a granulating agent, a coating agent and the like, to the extent of not impairing the purpose of the present invention.

The biofilm-removing agent and cleansing composition for hard surfaces of the present invention exert effects by contacting an aqueous solution of the agent or composition with the surface on which a biofilm has been formed. Examples of these methods include immersion, coating, spraying and the like. Furthermore, physical force may be applied with a sponge, a towel, a brush, a water jet or the like. The time necessary for the biofilm-removing agent to stay active varies depending on the amount of attached biofilms, the concentration at which the biofilm-removing agent is allowed to act, the operating temperature, and the presence or absence of physical force, but the time is in the range of several seconds to several hours. Furthermore, after the action, it is preferable to rinse off the removed biofilm by means of flowing water or the like.

The product of the present invention can be used in a wide range of fields where the damage brought about by biofilms is of concern. For example, the product of the present invention can be applied to cleansing agents for food manufacturing or beverage manufacturing plants, kitchens, cooking rooms, bathrooms, toilet bowls, the drainage ditches and drain pipes of kitchens, cooking rooms or the like, where the risk of bacterial contamination is high. The product of the present invention can also be applied to cooling water systems such as industrial cooling towers, desalting apparatuses, pulp and paper manufacturing systems, or circulating water systems such as baths, pools and artificial ponds. The product of the present invention can also be applied to the cleaners for medical instruments where biofilms easily form, for example, endoscopes, catheters, artificial dialyzers and the like. Furthermore, since the product of the present invention has high stability, the product can also be used in cleaners, toothpastes, oral care agents, denture care agents, contact lens cleaners and the like, which are intended for human body.

The cleansing composition for medical instruments of the present invention contains the basic amino acid derivative represented by the formula (1) or a salt thereof.

Here, the medical instruments may be those having the high possibility that the body fluid adheres thereto, such as endoscopes, catheters and artificial dialyzers (particularly, the circuit of artificial dialysate). Examples of the endoscopes include laryngendoscope, bronchoscope, upper gastrointestinal endoscope, small intestine endoscope, large intestine endoscope, thoracoscope, laparoscope, cystoscope, cholangioscope, arthroscope and angioscope.

The application areas of these endoscopes have expanded in recent years. The cleansing composition of the present invention is useful, especially for cleansing these endoscopes.

Examples of the use of the cleansing composition for medical instruments include a method of immersing a medical instrument in a cleansing composition for medical instruments; a method of contacting a medical instrument with an aqueous solution of the cleaner composition by placing a medical instrument within a water jet of the aqueous solution or while applying ultrasonic vibration; and the like. When a cleansing composition for medical instruments is used after being diluted, it is preferable to use an aqueous solution at a concentration of 0.2 to 20%, preferably 0.3 to 15% by weight, and more preferably 0.4 to 12% by weight.

EXAMPLES

Production Example 1

Production of N-[2-hydroxy-3-(2-ethylhexyl)oxypropyl]-L-arginine hydrochloride

In a four-necked 200-mL flask equipped with a reflux cooling tube, a dropping funnel, a thermometer and a stirring blade, 9.4 g (53.7 mmol) of L(+)-arginine, 50.0 g of water and 50.0 g of ethanol were placed, and the mixture was heated to 78° C. while being stirred under a nitrogen atmosphere. Subsequently, the inside of the reaction system was maintained at 78 to 80° C., 10.0 g (53.7 mmol) of 2-ethylhexyl glycidyl ether was added dropwise thereto. Thereafter, the mixture was aged for 4 hours at 78 to 80° C., and then was returned to room temperature. Subsequently, 9.8 g (53.7 mmol) of a 6 mol/L aqueous solution of hydrochloric acid was added thereto to neutralize the mixture. Water and ethanol were completely distilled off from the reaction solution under reduced pressure, and thus 21.6 g of N-[2-hydroxy-3-(2-ethylhexyl)oxypropyl]-L-arginine hydrochloride was obtained as a white solid. This compound corresponds to the compound 2 of Table 1.

Compounds having C10 (isodecyl) and C12 (liner-chain) were produced by the same method. These compounds correspond to the compound 3 and compound 4 of Table 1, respectively.

Example 1

Assay of Biofilm-Removing Ability

*Pseudomonas aeruginosa* (NBRC13275), *Serratia marcescens* (NBRC12648) and *Klebsiella pneumoniae* (ATCC13883) were each subjected to preculture for 24 hours at 37° C. using soybean-casein digest agar [SCD agar medium: manufactured by Nihon Pharmaceutical Co., Ltd.] to form colonies. A trace amount of bacterial mass obtained from the colonies of each species was inoculated using a sterilized bamboo skewer into a 24-well microplate added with 1.5 mL of Mueller-Hinton medium. This was cultured for 24 hours at 37° C., and then the culture fluid was disposed. Each of the wells was rinsed five times with 2 mL of purified water, and thus a biofilm was formed and attached to the microplate walls. Immediately, 2 mL each of the blend products containing prepared biofilm-removing agents indicated in Tables 2 and 3 (inventive products 1 to 24 and comparative products 1 to 19 as control) were added to exert the action for 10 minutes at room temperature, and then the biofilm control agent in each well was disposed. Each well was rinsed twice with 2 mL of purified water, and the 2 mL of 0.1 Crystal Violet was added thereto to stain the biofilm remaining on the microplate walls. Any excess of the staining solution was rinsed off with water, and then 2 mL of 80% ethanol was added to uniformly dissolve the Crystal Violet that had stained the biofilm. Then, the absorbance at 570 nm was measured as a measured value. Similarly, the wells upon which the biofilm-removing agent was not allowed to act were treated with 0.1% Crystal Violet, and then the absorbance was measured as the initial value. Furthermore, among the 24 wells, those that had been added with 1.5 mL of Mueller-Hinton medium but not inoculated with a bacterial mass were treated in the same manner, and the absorbance was measured as the blank value. An average value obtained by conducting each test five times was used. The removal rate was calculated by the following expression. The concentration in the table indicates the concentration of active ingredient based on the total amount (% by weight), and the pH was adjusted using potassium hydroxide or hydrochloric acid as necessary.

Removal rate (%)=100×[{(Initial value−Blank value)−(Measured value−Blank value)}/(Initial value−Blank value)]

The obtained biofilm removal rates are shown in Tables 2 and 3.

Compounds 1 to 5 in Tables 2 and 3 are those shown in Table 1 presented below, respectively.

TABLE 1

$$R^1-X-NH-\underset{\underset{COOH}{|}}{CH}-(CH_2)_m-Y \quad (1)$$

| | R1 | X | Y |
|---|---|---|---|
| Compound 1 *1 | C12,14 (Linear-chain) | OCH2CH(OH)CH2 | NHC(NH2)NH2+Cl− |
| Compound 2 | C8 (2-Ethylhexyl) | OCH2CH(OH)CH2 | NHC(NH2)NH2+Cl− |
| Compound 3 | C10 (Isodecyl) | OCH2CH(OH)CH2 | NHC(NH2)NH2+Cl− |
| Compound 4 | C12 (Linear-chain) | OCH2CH(OH)CH2 | NHC(NH2)NH2+Cl− |
| Compound 5 *2 | C12 (Linear-chain) | C=O | NHC(NH2)NH2+Cl− |

*1 Amisafe LMA-60 (manufactured by Ajinomoto Co., Inc.)
*2 Amisafe LA-01 (manufactured by Ajinomoto Co., Inc.)

TABLE 2

| Incorporated components (% by weight) | | Inventive product | | | | | | | | |
|---|---|---|---|---|---|---|---|---|---|---|
| | | 1 | 2 | 3 | 4 | 5 | 6 | 7 | 8 | 9 |
| Compound 1 *1 | | 1.0 | 0.5 | 0.2 | 0.1 | 0.02 | 0.01 | | | |
| Compound 2 | | | | | | | | 0.5 | | |
| Compound 3 | | | | | | | | | 0.5 | |
| Compound 4 | | | | | | | | | | 0.5 |
| L-arginine | | | | | | | | | | |
| L-arginine hydrochloride *2 | | | | | | | | | | |
| Urea | | | | | | | | | | |
| Na hypochlorite (in terms of effective chlorine concentration) | | | | | | | | | | |
| EDTA-2Na *3 | | | | | | | | | | |
| Nonionic surfactant 1 *4 | | | | | | | | | | |
| Anionic surfactant 1 *5 | | | | | | | | | | |
| Amphoteric surfactant 1 *6 | | | | | | | | | | |
| Purified water | | Balance | Balance | Balance | Balance | Balance | Balance | Balance | Balance | Balance |
| pH | | 4.6 | 4.6 | 4.6 | 4.6 | 4.6 | 4.6 | 4.6 | 4.6 | 4.6 |
| Biofilm removal rate (%) | Pseudomonas aeruginosa | 100 | 100 | 100 | 97 | 82 | 80 | 81 | 97 | 100 |
| | Serratia marcescens | 100 | 99 | 97 | 94 | 84 | 82 | 87 | 100 | 100 |
| | Staphylococcus epidermidis | 100 | 100 | 98 | 95 | 80 | 80 | 86 | 100 | 99 |

| Incorporated components (% by weight) | Comparative product | | | | | | | |
|---|---|---|---|---|---|---|---|---|
| | 1 | 2 | 3 | 4 | 6 | 7 | 8 | 9 |
| Compound 1 *1 | | | | | | | | |
| Compound 2 | | | | | | | | |
| Compound 3 | | | | | | | | |
| Compound 4 | | | | | | | | |
| L-arginine | 1.0 | | | | | | | |
| L-arginine | | 1.0 | | | | | | |

TABLE 2-continued

| | | | | | | | | | |
|---|---|---|---|---|---|---|---|---|---|
| hydrochloride *2 | | | | | | | | | |
| Urea | | | 1.0 | | | | | | |
| Na hypochlorite (in terms of effective chlorine concentration) | | | | 1.0 | | | | | |
| EDTA-2Na *3 | | | | | | 1.0 | | | |
| Nonionic surfactant 1 *4 | | | | | | | 1.0 | | |
| Anionic surfactant 1 *5 | | | | | | | | 1.0 | |
| Amphoteric surfactant 1 *6 | | | | | | | | | 1.0 |
| Purified water | | Balance | Balance | Balance | Balance | Balance | Balance | Balance | Balance |
| pH | | 10.8 | 4.5 | 8.0 | 12.0 | 4.5 | 6.0 | 7.5 | 7.5 |
| Biofilm removal rate (%) | Pseudomonas aeruginosa | 25 | 12 | 23 | 44 | 30 | 36 | 45 | 41 |
| | Serratia marcescens | 22 | 14 | 15 | 48 | 24 | 28 | 34 | 39 |
| | Staphylococcus epidermidis | 18 | 26 | 14 | 40 | 26 | 29 | 40 | 30 |

*1 N-[3-alkyl (C12,C14)oxy-2-hydroxypropyl]-L-arginine hydrochloride: Amisafe LMA-60 [manufactured by Ajinomoto Co., Inc.]
*2 A product obtained by neutralizing L-arginine with hydrochloric acid
*3 EDTA-2Na•dihydrate: reagent [manufactured by Wako Pure Chemical Industries, Ltd.]
*4 Polyoxyethylene (12) lauryl ether: Emulgen 120 [manufactured by Kao Corporation]
*5 Sodium lauryl sulfate: Emal-O [manufactured by Kao Corporation]
*6 Lauryldimethylamine oxide: Amphitol 20N [manufactured by Kao Corporation]

From the results shown above, it can be seen that biofilms are satisfactorily removed by using the biofilm-removing agent of the present invention.

Example 2

Test on the Cleansing Power Against Bathtub Contaminants

Test pieces made of polypropylene and each having a size of 80 mm in length×20 mm in width×1 mm in thickness were installed at the drainage ditch of a bathroom in a home for a 4-membered family, and were left untouched for two months. Subsequently, the test pieces were removed and were used as specimens to evaluate the cleansing power as follows. Cotton cloth pieces having the same size as the test piece were impregnated respectively with 3 mL each of the cleansing compositions as shown in Table 3 (Inventive products 10 to 24 and Comparative products 10 to 19 as control), and each of the specimens was adhered with one of the cotton cloth pieces for 5 minutes and then was rubbed with a sponge. Then, the state of soiling was visually evaluated on the basis of the following 5 grades, and the results for the cleansing power against bathtub contaminants, which are the average values of 5 tests, are presented in Table 3.

5: Removal of contaminants is very satisfactory.
4: Removal of contaminants is satisfactory.
3: Removal of contaminants lacks in uniformity.
2: Removal of contaminants is slightly recognizable.
1: Removal of contaminants is scarcely recognizable.

Example 3

Test on the Cleansing Power Against Kitchen Contaminants

Test pieces made of stainless steel and each having a size of 80 mm in length×20 mm in width×1 mm in thickness were installed at the drainage ditch of a kitchen in a home for a 4-membered family, and were left untouched for two months. Subsequently, the test pieces were removed and were used as specimens to evaluate the cleansing power as follows. Cotton cloth pieces having the same size as the test piece were impregnated respectively with 3 mL each of the cleansing compositions as shown in Table 3 (Inventive products 10 to 24 and Comparative products 10 to 19 as control), and each of the specimens was adhered with one of the cotton cloth pieces for 5 minutes and then was rubbed with a sponge. Then, the state of soiling was visually evaluated on the basis of the following 5 grades, and the results for the cleansing power against kitchen contaminants, which are the average values of 5 tests, are presented in Table 3.

5: Removal of contaminants is very satisfactory.
4: Removal of contaminants is satisfactory.
3: Removal of contaminants lacks in uniformity.
2: Removal of contaminants is slightly recognizable.
1: Removal of contaminants is hardly recognizable.

TABLE 3

| Incorporated component | Inventive product | | | | | | | | | | | | |
|---|---|---|---|---|---|---|---|---|---|---|---|---|---|
| (% by weight) | 10 | 11 | 12 | 13 | 14 | 15 | 16 | 17 | 18 | 19 | 20 | 21 | 22 |
| Compound 1 *1 | 5.00 | 2.00 | 0.20 | 2.00 | 2.00 | 2.00 | 2.00 | 2.00 | 2.00 | 2.00 | 2.00 | | |
| Compound 2 | | | | | | | | | | | | 8.00 | |
| Compound 3 | | | | | | | | | | | | | 2.00 |
| Compound 4 | | | | | | | | | | | | | |
| Compound 5 | | | | | | | | | | | | | |

TABLE 3-continued

| Incorporated component (% by weight) | | | | | | | | | | | | | |
|---|---|---|---|---|---|---|---|---|---|---|---|---|---|
| Sodium hydroxide | | | | | | | | | | | | | |
| Na hypochlorite (in terms of effective chlorine concentration) | | | | | | | | | | | | | |
| L-arginine | | | | | | | | | | | | | |
| L-arginine hydrochloride *2 | | | | | | | | | | | | | |
| EDTA-2Na *3 | | | | | | | | | 0.2 | 0.5 | | | |
| Nonionic surfactant 1 *4 | 2.0 | | | | 10.0 | 5.0 | 0.5 | | | | | | |
| Nonionic surfactant 2 *7 | | 2.0 | | 2.0 | | | | 4.0 | | | 2.0 | | |
| Anionic surfactant 1 *5 | | | 2.0 | | | | | | | | | | |
| Anionic surfactant 2 *8 | | | | 1.0 | | | | | 1.0 | | | | |
| Amphoteric surfactant 1 *6 | | | | | | | | | 0.5 | | | | 5.0 |
| Amphoteric surfactant 2 *9 | | | | 1.0 | | | | | 1.0 | | | | |
| Cationic surfactant *10 | | | | | 0.5 | | | | | | | | |
| Purified water | Balance | Balance | Balance | Balance | Balance | Balance | Balance | Balance | Balance | Balance | Balance | Balance | Balance |
| PH | 4.5 | 4.5 | 4.5 | 6.5 | 4.5 | 7.8 | 6.5 | 4.5 | 6.5 | 6.5 | 4.5 | 5.0 | 5.0 |
| Biofilm removal rate (%) Pseudomonas aeruginosa | 100 | 100 | 96 | 100 | 100 | 100 | 100 | 100 | 100 | 100 | 100 | 82 | 98 |
| Serratia marcescens | 100 | 100 | 98 | 100 | 100 | 100 | 100 | 100 | 100 | 100 | 100 | 84 | 96 |
| Staphylococcus epidermidis | 100 | 100 | 96 | 100 | 100 | 100 | 100 | 100 | 100 | 100 | 100 | 80 | 100 |
| Cleansing power against bathtub contaminants | 4.8 | 4.6 | 4.8 | 4.8 | 4.6 | 4.8 | 4.8 | 4.4 | 4.6 | 4.4 | 3.6 | 4.0 | 4.6 |
| Cleansing power against kitchen contaminants | 4.6 | 4.6 | 4.6 | 4.8 | 4.6 | 5.0 | 4.8 | 4.4 | 4.4 | 4.4 | 3.8 | 4.2 | 4.4 |

| Incorporated component | Inventive product | | Comparative product | | | | | | | | | |
|---|---|---|---|---|---|---|---|---|---|---|---|---|
| (% by weight) | 23 | 24 | 10 | 11 | 12 | 13 | 14 | 15 | 16 | 17 | 18 | 19 |
| Compound 1 *1 | | | | | | | | | | | | |
| Compound 2 | | | | | | | | | | | | |
| Compound 3 | | | | | | | | | | | | |
| Compound 4 | 2.00 | | | | | | | | | | | |
| Compound 5 | | 0.2 | | | | | | | | | | |
| Sodium hydroxide | | | | | | | | | 0.02 | 0.05 | | |
| Na hypochlorite (in terms of effective chlorine concentration) | | | | | | | | | 1.0 | 1.0 | | |
| L-arginine | | | | | | | | | | | | |
| L-arginine hydrochloride *2 | | | | | | | | | | | 2.0 | |
| EDTA-2Na *3 | | | | | 0.2 | 0.5 | 0.5 | | | | | 2.0 |
| Nonionic surfactant 1 *4 | | 10.0 | 7.0 | | | | | | | | | 10.0 |
| Nonionic surfactant 2 *7 | | | | | | 5.0 | | 3.0 | | | 2.0 | |
| Anionic surfactant 1 *5 | | | | 2.0 | | | | | 0.5 | | | |
| Anionic surfactant 2 *8 | | | | | | | 1.0 | 2.0 | | | | |
| Amphoteric surfactant 1 *6 | | | | | 1.5 | | | | | 0.5 | | |
| Amphoteric surfactant 2 *9 | 2.0 | | | | | 1.0 | 2.0 | | | | | |
| Cationic surfactant *10 | | | | | | | | 1.5 | | | | |
| Purified water | Balance | Balance | Balance | Balance | Balance | Balance | Balance | Balance | Balance | Balance | Balance | Balance |
| PH | 5.0 | 5.0 | 4.5 | 4.5 | 4.5 | 6.5 | 4.5 | 4.5 | 11.0 | 13.0 | 10.5 | 4.5 |
| Biofilm removal rate (%) Pseudomonas aeruginosa | 100 | 74 | 40 | 35 | 33 | 25 | 16 | 51 | 55 | 45 | 31 | 34 |
| Serratia marcescens | 100 | 71 | 46 | 26 | 35 | 21 | 24 | 49 | 62 | 64 | 28 | 32 |
| Staphylococcus epidermidis | 100 | 68 | 38 | 38 | 34 | 24 | 26 | 42 | 62 | 54 | 33 | 30 |
| Cleansing power against bathtub contaminants | 4.8 | 3.6 | 2.2 | 2.6 | 4.0 | 4.2 | 4.2 | 1.6 | 2.2 | 2.8 | 2.0 | 2.4 |
| Cleansing power against kitchen contaminants | 4.6 | 3.6 | 3.8 | 2.2 | 2.2 | 2.0 | 2.2 | 1.8 | 4.4 | 4.2 | 2.2 | 2.0 |

*1 N-[3-alkyl (C12,C14)oxy-2-hydroxypropyl]-L-arginine hydrochloride: Amisafe LMA-60 [manufactured by Ajinomoto Co., Inc.]
*2 A product obtained by neutralizing L-arginine with hydrochloric acid
*3 EDTA-2Na·dihydrate: reagent [manufactured by Wako Pure Chemical Industries, Ltd.]
*4 Polyoxyethylene (12) lauryl ether: Emulgen 120 [manufactured by Kao Corporation]
*5 Sodium lauryl sulfate: Emal-O [manufactured by Kao Corporation]
*6 Lauryldimethylamine oxide: Amphitol 20N [manufactured by Kao Corp.]
*7 Lauryl glycoside: Mydol 12 [manufactured by Kao Corporation]
*8 Sodium polyoxyethylene lauryl ether sulfate: Emal 20C [manufactured by Kao Corporation]
*9 Laurylhydroxysulfobetaine: Amphitol 20HD [manufactured by Kao Corporation]
*10 Cetyltrimethylammonium chloride: Coatamin 60W [manufactured by Kao Corporation]

Example 4

Test on Biofilm Removal from Teflon (Registered Trademark) Tube

Pseudomonas aeruginosa (NBRC13275) and Klebsiella pneumoniae (ATCC13883) were subjected to preculture for 24 hours at 37° C. using soybean-casein digest agar [SCD agar medium: manufactured by Nihon Pharmaceutical Co., Ltd.].

One platinum loop of the resulting bacterial colony of each species on the agar medium was inoculated, and a culture fluid prepared by suspending the bacterial cells was circulated through a Teflon (registered trademark) tube (inner diameter 5 mm, outer diameter 7 mm) for 48 hours at 30° C. at a flow rate of 50 to 60 mL/min, using a Masterflex quantitative pump system (system model No. 7553-80, head No. 7016-21) manufactured by Cole-Parmer Instrument Company, to thereby form a biofilm on the inner surface of the Teflon (registered trademark) tube. The culture fluid was disposed, and the compositions shown in Tables 2 and 3 were prepared at a 10% concentration with sterilized purified water. These liquids were circulated at 30° C. at a flow rate of 50 to 60 mL/min, and before the treatment and 30 minutes after the treatment, the biofilm attached to the inside of the Teflon (registered trademark) tube was stained with 0.1% Crystal Violet and was checked by visual inspection. The state of biofilm formation was evaluated such that an amount of 0 to 10% of the amount of biofilm attachment in the control was graded as "A", an amount of 10 to 40% as "B", an amount of 40 to 80% as "C", and an amount of 80% or more as "D".

The results are presented in Table 4.

TABLE 4

| | | Control | Invented product | | | | Comparative product | | | |
|---|---|---|---|---|---|---|---|---|---|---|
| | | | 2 | 4 | 12 | 19 | 10 | 13 | 17 | 19 |
| State of biofilm attachment | Before treatment | D | D | D | D | D | D | D | D | D |
| | 30 minutes after treatment | D | A | A | A | A | D | D | D | D |

From the results shown above, the biofilm-removing effect of the invented product of the present invention is obvious. The Teflon (registered trademark) tube is a product used for endoscopic applications, and therefore, it can be seen from the effect that the present invention is excellent in the biofilm-removing effect for endoscopic applications.

Example 5

Assay of Biofilm-Removing Ability

Pseudomonas aeruginosa (NBRC13275), Serratia marcescens (NBRC12648) and Klebsiella pneumoniae (ATCC13883) were respectively subjected to preculture for 24 hours at 37° C. using soybean-casein digest agar [SCD agar medium: manufactured by Nihon Pharmaceutical Co., Ltd.] to form colonies. A trace amount of bacterial mass obtained from the colonies of each species was inoculated using a sterilized bamboo skewer into a 24-well microplate added with 1.5 mL of Mueller-Hinton medium. This was cultured for 24 hours at 37° C., and then the culture fluid was disposed. Each of the wells was rinsed five times with 2 mL of purified water, and thus a biofilm was formed and attached to the microplate walls. Immediately, liquids prepared by diluting the prepared blend products (invented products 25 to 39 and comparative products 20 to 24 as control) to a 10-fold volume with purified water were added in an amount of 2 mL each, and the products were allowed to act for 10 minutes at room temperature. Then, the biofilm control agent in each well was disposed. Each of the wells was rinsed two times with 2 mL of purified water, and then 2 mL of 0.1% Crystal Violet was added to stain the biofilm remaining on the microplate wall. Any excess of the staining solution was rinsed off with water, and then 2 mL of 80% ethanol was added to uniformly dissolve the Crystal Violet that had stained the biofilm. Then, the absorbance at 570 nm was measured as a measured value. Similarly, the wells upon which the cleansing composition for hard surfaces was not allowed to act were treated with 0.1% Crystal Violet, and then the absorbance was measured as the initial value. Furthermore, among the 24 wells, those that had been added with 1.5 mL of Mueller-Hinton medium but not inoculated with a bacterial mass were treated in the same manner, and the absorbance was measured as the blank value. An average value obtained by conducting each test five times was used. The removal rate was calculated by the following expression. The concentration in the table indicates the concentration of active ingredient based on the total amount (% by weight), and the pH was adjusted using potassium hydroxide or citric acid as necessary.

Removal rate (%)=100×[{(Initial value−Blank value)−(Measured value−Blank value)}/(Initial value−Blank value)]

The obtained biofilm removal rates are presented in Table 5.

Compounds 1 to 4 in the table are the compounds shown in the Table 1.

TABLE 5

| Incorporated component | | Inventive product | | | | | | | | | |
|---|---|---|---|---|---|---|---|---|---|---|---|
| | (% by weight) | 25 | 26 | 27 | 28 | 29 | 30 | 31 | 32 | 33 | 34 |
| Component (A) | Compound 1 *1 | 2.0 | 2.0 | 2.0 | 2.0 | 2.0 | 2.0 | 2.0 | 2.0 | 2.0 | 10.0 |
| | Compound 2 | | | | | | | | | | |
| | Compound 3 | | | | | | | | | | |
| | Compound 4 | | | | | | | | | | |
| Component (B) | Sodium hydroxide | 2.0 | | | 1.0 | 1.0 | 4.5 | | 4.5 | | |
| | Potassium hydroxide | | 2.0 | | 1.0 | | | 4.5 | | 2.0 | |
| | Monoethanolamine | | | 5.0 | | 4.0 | | | 3.0 | 3.0 | 8.3 |

TABLE 5-continued

| Incorporated component | | Inventive Product | | | | | | | | | |
|---|---|---|---|---|---|---|---|---|---|---|---|
| (% by weight) | | | | | | | | | | | |
| Component (C) | Nonionic surfactant 1 *2 | 10.0 | | | | 5.0 | | 5.0 | | | 10.0 |
| | Nonionic surfactant 2 *3 | | 5.0 | | | | | | | | |
| | Anionic surfactant 1 *4 | | | 10.0 | | | | | | | |
| | Anionic surfactant 2 *5 | | | | 5.0 | | | 5.0 | 5.0 | | |
| | Amphoteric surfactant 1 *6 | | | | | | 9.0 | | | 10.0 | |
| | Amphoteric surfactant 2 *7 | | | | | 5.0 | | | 5.0 | | |
| | Cationic surfactant *8 | | | | | | 1.0 | | | | |
| Component (D) | EDTA-4Na *9 | | | | | | | 5.0 | | | |
| | NTA-3Na *10 | | | | | | | | 5.0 | | |
| | Citric acid *11 | | | | | | | | | | 9.0 |
| Other component | Na hypochlorite (in terms of effective chlorine concentration) | | | | | | | | | | |
| | Purified water | Balance | Balance | Balance | Balance | Balance | Balance | Balance | Balance | Balance | Balance |
| | PH | 11.0 | 11.0 | 10.5 | 11.0 | 11.0 | 12.0 | 11.8 | 12.2 | 11.0 | 9.0 |
| Biofilm removal rate (%) (tested with 10-fold dilution) | *Pseudomonas aeruginosa* | 100 | 100 | 100 | 100 | 100 | 100 | 100 | 100 | 100 | 100 |
| | *Serratia marcescens* | 100 | 100 | 100 | 100 | 100 | 100 | 100 | 100 | 100 | 100 |
| | *Staphylococcus epidermidis* | 100 | 100 | 100 | 100 | 100 | 100 | 100 | 100 | 100 | 100 |
| | Cleansing power against bathtub contaminants | 4.8 | 4.6 | 4.8 | 4.8 | 4.6 | 4.6 | 4.8 | 4.8 | 4.8 | 4.4 |
| | Cleansing power against kitchen contaminants | 4.6 | 4.6 | 4.6 | 4.8 | 4.6 | 4.8 | 4.4 | 5.0 | 4.8 | 4.4 |
| | Cleansing power against toilet bowl contaminants | B | B | A | B | A | A | A | A | A | A |

| Incorporated component | | Inventive Product | | | | | Comparative product | | | | |
|---|---|---|---|---|---|---|---|---|---|---|---|
| (% by weight) | | 35 | 36 | 37 | 38 | 39 | 20 | 21 | 22 | 23 | 24 |
| Component (A) | Compound 1 *1 | 5.0 | 0.2 | | | | | | | | |
| | Compound 2 | | | 2.0 | | | | | | | |
| | Compound 3 | | | | 2.0 | | | | | | |
| | Compound 4 | | | | | 2.0 | | | | | |
| Component (B) | Sodium hydroxide | 2.0 | | 2.0 | | | 2.0 | 4.5 | | 0.02 | 0.05 |
| | Potassium hydroxide | | 2.0 | | 2.0 | | | | | | |
| | Monoethanolamine | | | | | 2.0 | | 3.0 | 8.3 | | |
| Component (C) | Nonionic surfactant 1 *2 | 10.0 | 10.0 | | 5.0 | | 10.0 | | 10.0 | | |
| | Nonionic surfactant 2 *3 | | | 3.0 | | | | | | 0.5 | |
| | Anionic surfactant 1 *4 | | | | | 5.0 | | | | | |
| | Anionic surfactant 2 *5 | | | | | | | 5.0 | | | |
| | Amphoteric surfactant 1 *6 | | | | | | | | | | 0.5 |
| | Amphoteric surfactant 2 *7 | | | | | | | 5.0 | | | |
| | Cationic surfactant *8 | | | | | | | | | | |
| Component (D) | EDTA-4Na *9 | | | | | | | 5.0 | | | |
| | NTA-3Na *10 | | | | | | | | | | |
| | Citric acid *11 | | | | | | | | 9.0 | | |
| Other component | Na hypochlorite (in terms of effective chlorine concentration) | | | | | | | | | 1.0 | 1.0 |
| | Purified water | Balance | Balance | Balance | Balance | Balance | Balance | Balance | Balance | Balance | Balance |
| | PH | 11.0 | 11.0 | 11.0 | 11.0 | 11.0 | 11.0 | 12.2 | 9.0 | 11.0 | 13.0 |
| Biofilm removal rate (%) (tested with 10-fold dilution) | *Pseudomonas aeruginosa* | 100 | 96 | 93 | 99 | 100 | 40 | 35 | 33 | 44 | 36 |
| | *Serratia marcescens* | 100 | 98 | 90 | 100 | 100 | 46 | 26 | 35 | 52 | 54 |
| | *Staphylococcus epidermidis* | 100 | 97 | 95 | 100 | 100 | 38 | 38 | 34 | 50 | 41 |
| | Cleansing power against bathtub contaminants | 4.6 | 4.4 | 4.4 | 4.8 | 4.6 | 2.2 | 2.6 | 4.0 | 2.1 | 2.2 |
| | Cleansing power against kitchen contaminants | 4.4 | 4.4 | 4.2 | 4.6 | 4.8 | 3.8 | 2.2 | 2.2 | 3.8 | 3.2 |
| | Cleansing power against toilet bowl contaminants | B | B | B | A | A | C | C | C | C | C |

*1 N-[3-alkyl (12,14)oxy-2-hydroxypropyl]-L-arginine hydrochloride: Amisafe LMA-60 [manufactured by Ajinomoto Co., Inc.]
*2 Polyoxyethylene (12) lauryl ether: Emulgen 120 [manufactured by Kao Corp.]
*3 Sodium lauryl sulfate: Emal-O [manufactured by Kao Corporation]
*4 Lauryldimethylamine oxide: Amphitol 20N [manufactured by Kao Corp.]
*5 Lauryl glycoside: Mydol 12 [manufactured by Kao Corporation]
*6 Sodium polyoxyethylene lauryl ether sulfate: Emal 20C [manufactured by Kao Corporation]
*7 Laurylhydroxysulfobetaine: Amphitol 20HD [manufactured by Kao Corporation]
*8 Cetyltrimethylammonium chloride: Coatamin 60W [manufactured by Kao Corporation]
*9 EDTA-4Na·dihydrate: reagent [manufactured by Wako Pure Chemical Industries, Ltd.]
*10 NTA-3Na·monohydrate: reagent [manufactured by Wako Pure Chemical Industries, Ltd.]
*11 Citric acid: reagent [manufactured by Wako Pure Chemical Industries, Ltd.]

From the results shown above, it can be seen that biofilms are satisfactorily removed by using the cleansing composition for hard surfaces of the present invention.

Example 6

Test on the Cleaning Power Against Bathtub Contaminants

Test pieces made of polypropylene and each having a size of 80 mm in length×20 mm in width×1 mm in thickness were installed at the drainage ditch of a bathroom in a home for a 4-membered family, and were left untouched for two months. Subsequently, the test pieces were removed and were used as specimens to evaluate the cleansing power as follows. Cotton cloth pieces having the same size as the test piece were impregnated respectively with 3 mL each of test liquids obtained by diluting the cleansing compositions for hard surfaces as shown in Table 5 (Inventive products 25 to 39 and Comparative products 20 to 24 as control) to a 10-fold volume with purified water, and each of the specimens was adhered with one of the cotton cloth pieces for 1 minute and then was rubbed with a sponge. Then, the state of soiling was visually evaluated on the basis of the following 5 grades, and the results for the cleansing power against bathtub contaminants, which are the average values of 5 tests, are presented in Table 5.
- 5: Removal of contaminants is very satisfactory.
- 4: Removal of contaminants is satisfactory.
- 3: Removal of contaminants lacks in uniformity.
- 2: Removal of contaminants is slightly recognizable.
- 1: Removal of contaminants is hardly recognizable.

Example 7

Test on the Cleansing Power Against Kitchen Contaminants

Test pieces made of stainless steel and each having a size of 80 mm in length×20 mm in width×1 mm in thickness were installed at the drainage ditch of a kitchen in a home for a 4-membered family, and were left untouched for two months. Subsequently, the test pieces were removed and were used as specimens to evaluate the cleansing power as follows. Cotton cloth pieces having the same size as the test piece were impregnated respectively with 3 mL each of test liquids obtained by diluting the cleansing compositions for hard surfaces as shown in Table 5 (Inventive products 25 to 39 and Comparative products 20 to 24 as control) to a 10-fold volume with purified water, and each of the specimens was adhered with one of the cotton cloth pieces for 1 minute and then was rubbed with a sponge. Then, the state of soiling was visually evaluated on the basis of the following 5 grades, and the results for the cleansing power against kitchen contaminants, which are the average values of 5 tests, are presented in Table 3.
- 5: Removal of contaminants is very satisfactory.
- 4: Removal of contaminants is satisfactory.
- 3: Removal of contaminants lacks in uniformity.
- 2: Removal of contaminants is slightly recognizable.
- 1: Removal of contaminants is hardly recognizable.

Example 8

Test on the Cleansing Power Against Toilet Bowl Contaminants

The cleansing power against a complex of inorganic and organic contaminants in the inner side of a flush toilet bowl, which is not removable by just rubbing with a brush, was evaluated as follows. 10 mL each of test liquids obtained by diluting the cleansing compositions for hard surfaces as shown in Table 5 (Inventive products 25 to 39 and Comparative products 20 to 24 as control) to a 10-fold volume with purified water, were uniformly sprayed onto the contaminants and were left untouched for 5 minutes. Then, the state of removed contaminants after rubbing with a brush was visually evaluated as follows, and the results for cleansing power against toilet bowl contaminants are presented in Table 5.
- A: Good
- B: Slightly good
- C: Slightly poor
- D: Poor As shown from Examples 6 to 8, it can be seen that the inventive products of the present invention exhibit excellent cleansing power against a complex of contaminants having biofilms in concomitance on hard surfaces, as compared with the comparative products 20 to 24, which are related art products modeled on commercially available detergents for bathtub contaminants, commercially available detergents for kitchen contaminants and commercially available detergents for toilet bowl contaminants.

The invention claimed is:

1. A method of removing a biofilm on a surface of a medical instrument selected from the group consisting of an endoscope, a catheter, an artificial dialyzer, and a circuit of an artificial dialyzer, comprising:
contacting a biofilm-removing agent with the biofilm, wherein said biofilm-removing agent comprises a basic amino acid derivative represented by the following formula (1) or a salt thereof:

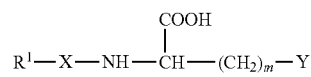

(1)

wherein $R^1$ represents a linear- or branched-alkyl group having 4 to 18 carbon atoms or a linear- or branched-alkenyl group having 4 to 18 carbon atoms; X and Y each represent a group selected from the groups represented by the following formulas:

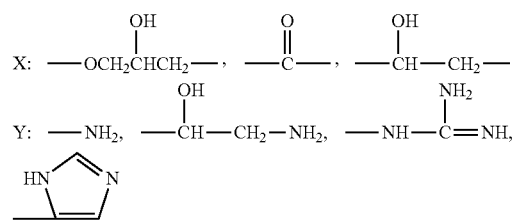

and m represents an integer from 1 to 5.

2. A method of removing a biofilm according to claim 1, wherein in the formula (1), m is 3, and Y is —NH—C(—NH$_2$)=NH.

3. A method of removing a biofilm according to claim 1, wherein in the formula (1), X is —OCH$_2$—CH(—OH)CH$_2$—.

4. A method of removing a biofilm according to claim 1, wherein the basic amino acid derivative represented by formula (1) or a salt thereof is present in a biofilm-removing composition, which composition also contains one or more members selected from the group consisting of surfactants, other than the basic amino acid derivative represented by formula (1) or a salt thereof, and chelating agents.

5. A method of removing a biofilm according to claim 1, wherein the basic amino acid derivative represented by formula (1) or a salt thereof is present in a biofilm-removing composition, which composition also contains an alkali agent, and a surfactant other than the basic amino acid derivative represented by formula (1) or a salt thereof.

6. A method of removing a biofilm according to claim 1, wherein a concentration of the amino acid derivative of formula (1) or the salt thereof in the biofilm-removing agent is 0.001 to 80% by weight.

7. A method of removing a biofilm according to claim 1, wherein the biofilm-removing agent is contained in an aqueous solution and is contacted with the biofilm by way of immersion, coating or spraying of a surface on which the biofilm is formed, and wherein physical force is optionally applied to the biofilm with a sponge, a towel, a brush, or a water jet.

8. A method of removing a biofilm according to claim 1, wherein the biofilm is contacted with the biofilm-removing agent containing the amino acid derivative of formula (1) or the salt thereof by immersing the medical instrument in an aqueous solution containing the biofilm-removing agent, or by placing the medical instrument in a water jet of an aqueous solution containing the biofilm-removing agent, or by immersing the medical instrument in an aqueous solution containing the biofilm-removing agent while applying ultrasonic vibration to the aqueous solution having the medical instrument immersed therein.

9. A method of removing a biofilm according to claim 8, wherein the medical instrument is an endoscope selected from the group consisting of a laryngendoscope, a bronchoscope, a upper gastrointestinal endoscope, a small intestine endoscope, a large intestine endoscope, a thoracoscope, a laparoscope, a cystoscope, a cholangioscope, an arthroscope and an angioscope.

10. A method of removing a biofilm according to claim 8, wherein the aqueous solution contains the amino acid derivative of formula (1) or a salt thereof in a concentration of 0.2 to 20% by weight.

11. A method of removing a biofilm according to claim 1, wherein the biofilm-removing agent containing the amino acid derivative of formula (1) or the salt thereof is present in an aqueous solution having a pH of 4.5 to 12.2.

12. A method of removing a biofilm according to claim 1, wherein the biofilm contains *Klebsiella pneumoniae, Pseudomonas aeruginosa, Serratia marcescens* or *Staphylococcus epidermidis*.

13. A method of removing a biofilm according to claim 8, wherein the biofilm-removing agent containing the amino acid derivative of formula (1) or the salt thereof is present in an aqueous solution having a pH of 4.5 to 12.2; and wherein the biofilm contains *Klebsiella pneumoniae, Pseudomonas aeruginosa, Serratia marcescens* or *Staphylococcus epidermidis*.

14. A method of removing a biofilm according to claim 1, wherein the biofilm-removing agent is in an aqueous solution having a pH of 4.5 to 12.2, wherein the amino acid derivative of formula (1) or the salt thereof is contained in the aqueous solution in a concentration of 0.2 to 20% by weight; and wherein the biofilm contains *Klebsiella pneumoniae, Pseudomonas aeruginosa, Serratia marcescens* or *Staphylococcus epidermidis*.

15. A method of removing a biofilm according to claim 8, wherein the biofilm-removing agent is in an aqueous solution having a pH of 4.5 to 12.2, wherein the amino acid derivative of formula (1) or the salt thereof is contained in the aqueous solution in a concentration of 0.2 to 20% by weight; and wherein the biofilm contains *Klebsiella pneumoniae, Pseudomonas aeruginosa, Serratia marcescens* or *Staphylococcus epidermidis*.

16. A method of removing a biofilm according to claim 15, wherein the medical instrument is an endoscope selected from the group consisting of a laryngendoscope, a bronchoscope, a upper gastrointestinal endoscope, a small intestine endoscope, a large intestine endoscope, a thoracoscope, a laparoscope, a cystoscope, a cholangioscope, an arthroscope or an angioscope.

17. A method of removing a biofilm according to claim 1, wherein the biofilm-removing agent is contacted with the biofilm for one to ten minutes.

* * * * *